United States Patent
Ottoboni et al.

(10) Patent No.: US 8,460,637 B2
(45) Date of Patent: Jun. 11, 2013

(54) RECONSTITUTABLE MICROSPHERE COMPOSITIONS USEFUL AS ULTRASONIC CONTRAST AGENTS

(75) Inventors: Thomas B. Ottoboni, Belmont, CA (US); Robert E. Short, Los Gatos, CA (US)

(73) Assignee: University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/252,743

(22) Filed: Oct. 4, 2011

(65) Prior Publication Data

US 2012/0052016 A1 Mar. 1, 2012

Related U.S. Application Data

(63) Continuation of application No. 12/329,202, filed on Dec. 5, 2008, now abandoned, which is a continuation of application No. 10/977,100, filed on Oct. 28, 2004, now abandoned.

(60) Provisional application No. 60/517,219, filed on Oct. 31, 2003.

(51) Int. Cl.
*A61B 8/00* (2006.01)
(52) U.S. Cl.
USPC .......................................................... 424/9.5
(58) Field of Classification Search
USPC .......................................................... 424/9.5
See application file for complete search history.

(56) References Cited

U.S. PATENT DOCUMENTS

| | | | |
|---|---|---|---|
| 5,558,857 A | 9/1996 | Klaveness et al. | 424/9.52 |
| 5,565,215 A | 10/1996 | Gref et al. | 424/501 |
| 5,670,135 A | 9/1997 | Schroder | 424/9.5 |
| 5,674,468 A | 10/1997 | Klaveness et al. | 424/9.3 |
| 6,022,252 A | 2/2000 | Ozawa | 440/88 |
| 6,045,777 A | 4/2000 | Church et al. | 424/9.52 |
| 6,063,362 A | 5/2000 | Lohrmann | 424/9.52 |
| 6,123,922 A | 9/2000 | Bichon et al. | 424/9.52 |
| 6,139,819 A | 10/2000 | Unger et al. | 424/9.52 |
| 6,165,442 A | 12/2000 | Swaerd-Nordmo et al. | 424/9.52 |
| 6,177,062 B1 | 1/2001 | Stein et al. | 424/9.52 |
| 6,193,951 B1 * | 2/2001 | Ottoboni et al. | 424/9.5 |
| 6,200,548 B1 | 3/2001 | Bichon et al. | 424/9.51 |
| 6,264,959 B1 | 7/2001 | Stein et al. | 424/400 |
| 6,333,021 B1 | 12/2001 | Schneider et al. | 424/9.52 |
| 6,569,405 B1 | 5/2003 | Sutton et al. | 424/9.52 |
| 2003/0118649 A1 | 6/2003 | Gao et al. | 424/471 |

OTHER PUBLICATIONS

Langer et al.,(1983) "Chemical and physical structure of polymers as carriers for controlled release of bioactive agents: a review," Macromol. Chem. Phys. C23 (1), 61-125.
International Search Report—PCT/US2004/036537.

* cited by examiner

*Primary Examiner* — Daniel Sullivan
*Assistant Examiner* — Trevor Love
(74) *Attorney, Agent, or Firm* — Medlen & Carroll, LLP (57) ABSTRACT

Methods and suspensions are provided that are useful for preparing readily reconstitutable, dry compositions of micro- or nanospheres. The dry compositions find use in diagnostic applications such as ultrasonic imaging. The suspension includes as key ingredients one or both of t-butyl alcohol and/or an amorphous sugar (or mixture of amorphous sugar) in specified amounts that reduce aggregation of the particles comprising the suspension.

7 Claims, 8 Drawing Sheets

FIG. 1A
Peak Diameter

FIG. 1D
Volume % > 7 Microns

FIG. 2B
Mean Diameter

RECONSTITUTABLE MICROSPHERE COMPOSITIONS USEFUL AS ULTRASONIC CONTRAST AGENTS

RELATED APPLICATIONS

This application claims benefit of priority under 35 U.S.C. §119(e) to U.S. Provisional Patent Application No. 60/517,219 filed. Oct. 31, 2003, the disclosure of which is incorporated herein by reference in its entirety.

BACKGROUND

Solid and hollow-cored micro- and nano-particles are used in a growing variety of medical, pharmaceutical, and diagnostic applications. When injected into the bloodstream, such particles can be used as ultrasonic echographic imaging contrast agents to aid the visualization of internal structures, such as the heart and blood vessels. Such contrast agents may also be used to examine organ perfusion, for example, to assess the damage caused by an infarct, to examine organs such as the liver, or to differentiate between normal and abnormal tissues such as tumors and cysts.

Ultrasonic contrast is achieved when acoustic impedance between two materials at an interface is different. Ultrasonic imaging methods and particle compositions useful as contrast agents are described in greater detail in, for example, Ultrasound Contrast Agents, Basic Principles and Clinical Applications, Goldberg et al., Eds, 2d Edition, 2001, Martin Dunitz Ltd. Solid-cored particles (also called "matrix" particles) useful as ultrasound contrast agents are described in, for example, U.S. Pat. No. 5,558,857, U.S. Pat. No. 5,670,135, U.S. Pat. No. 5,674,468, U.S. Pat. No. 6,264,959, U.S. Pat. No. 6,177,062 and U.S. Pat. No. 5,565,215. Hollow-cored particles useful as contrast agents are described in, for example, U.S. Pat. No. 6,193,951, U.S. Pat. No. 6,200,548, U.S. Pat. No. 6,123,922, U.S. Pat. No. 6,333,021, U.S. Pat. No. 6,063,362, U.S. Pat. No. 6,022,252, U.S. Pat. No. 6,569,405, U.S. Pat. No. 6,045,777 and currently pending U.S. application Ser. No. 09/637,516. Both hollow- and solid-cored particles may also be used to deliver pharmaceutical products such as drugs and/or other therapeutic or diagnostic compositions to targeted organs or tissues in the body. Pharmaceuticals may be released from the particle by diffusion, by degradation of the particle, or by rupture of the particle in situ using ultrasonic energy.

A well-known stabilization method for injectable ultrasonic contrast agents as well as for pharmaceutical delivery particles is freeze-drying, also known as lyophilization. Various methods of freeze-drying and then stabilizing and storing a particle suspension have been previously described, for instance in U.S. Pat. No. 6,165,442. However, the particles in the suspension oftentimes aggregate during the lyophilization process (or upon storage). Such aggregation can be undesirable, especially in instances where the lyophilized particle composition will be administered to a patient via intravenous injection.

Aggregation problems are especially acute for particles composed of proteins, or particles having a proteinaceous outer coating. Aggregation problems can also be encountered with particles composed of synthetic polymers and/or mixtures of synthetic polymers and proteins. Other problems inherent in the preparation and lyophilization of injectable particles include removal of one or more of the organic solvents used in processing. This is particularly important in the formation and preparation of hollow-cored particle compositions.

Therefore, there is a need for methods for improved preparation and handling of compositions of lyophilized micro- and nano-particles to reduce aggregation and provide for more effectively and conveniently reconstituted compositions.

SUMMARY

These and other needs are addressed by the present invention, which in certain aspects provides particle suspensions and methods for making dry particle compositions that reduce the propensity of the particles to aggregate or "stick together" during lyophilization, storage, and reconstitution. Also provided are dry particle compositions that are readily dispersible upon reconstitution with water.

The invention is based, in part, on two important discoveries. First, the Applicants have discovered that adding a specified quantity of an amorphous sugar to a suspension of polymeric particles comprising a proteinaceous outer coating greatly reduces the propensity of the particles to stick together, especially during lyophilization of the particle suspension. However, it was observed that if the amorphous sugar is present in concentrations sufficient to reduce or avoid aggregation of the particles upon lyophilization or storage of the lyophilized particle composition, removal of the solvents used in the fabrication of the particles is impeded. Second, the Applicants have discovered that adding a specified quantity of t-butyl alcohol to a particle suspension comprising an amorphous sugar in what would otherwise have been a suboptimal concentration (low enough in concentration to allow good solvent removal but too low to completely inhibit aggregation) aids removal of solvents during lyophilization of the particle suspensions, and in particular aids the removal of solvents from the hollow core of hollow-cored particles and provides a stable, dry lyophilized particle composition with little or no aggregation of the particles. Dry particle compositions prepared from suspensions including the specified quantities of t-butyl alcohol and/or amorphous sugar are readily dispersed upon reconstitution with water, making them ideally suited for diagnostic and/or therapeutic applications. Because of this facile-dispersibility, dry particle compositions prepared by lyophilizing the particle suspensions described herein are especially suited for administration to animals and humans via intravenous injection.

Thus, in one aspect, the present invention provides aqueous suspensions of particles that are useful for preparing dry particle compositions suitable for reconstitution and in vivo administration to animals and humans that overcome the propensity of the particles to aggregate during lyophilization as compared to conventional suspensions. The suspension generally comprises from 0.3 to 4 mg of hollow-cored particles (weight is based upon the weight of the shell material) per milliliter (mL) of suspension or from 0.3 mg to 56 mg solid-cored particles per milliliter of suspension and one or both of the following: t-butyl alcohol and/or an amorphous sugar for a mixture of two or more amorphous sugars). The amounts of t-butyl alcohol and/or amorphous sugar(s) comprising the suspension will depend upon whether the suspension comprises hollow-cored particles or solid cored particles. For sold-cored particles, the suspension generally comprises t-butyl alcohol in a weight to weight ratio (t-butyl alcohol: particle) range of approximately 2.14:1 to 43:1 and/or an amorphous sugar (or mixture of amorphous sugars) in a weight to weight ratio (total amorphous sugar(s):particle) range of approximately 0.02:1 to 0.86:1. For hollow-cored particles, the suspension generally comprises t-butyl alcohol in a weight to weight ratio (t-butyl alcohol:particle) range of approximately 30:1 to 600:1 and/or an amorphous sugar (or mixture of amorphous sugars) in a weight to weight ratio (total amorphous sugar(s):particle) range of approximately 0.3:1 to 12:1.

In general, the bulk of the suspension is water. However, the suspension may include additional solvents, such as the solvents and/or solvent mixtures typically used during the preparation of the particles, and/or one or more excipients, such as, for example, buffering agents, agents to adjust osmolality and tonicity and bulking agents. The suspensions may also include one or more surfactants. However, a significant advantage of the suspensions described herein is the ability to handle and lyophilize the suspensions without significant aggregation of the particles. Thus, while the suspensions may include surfactants and other conventional anti-aggregation agents, the use of such agents is not necessary.

In one embodiment, the suspension includes both the t-butyl alcohol and the amorphous sugar(s).

In another aspect, the invention provides methods of making dry compositions of particles that are easily reconstitutable and dispersible upon addition of water. In one sense; the method comprises lyophilizing to dryness an aqueous particle suspension comprising t-butyl alcohol and/or one or more amorphous sugars, as described above. The t-butyl alcohol and/or amorphous sugars) (and any optional excipients and/ or surfactants) are typically added to a particle suspension after the formation of the polymeric and/or proteinaceous particles and prior to lyophilization. For example, solid-cored or hollow-cored particles can be prepared using conventional techniques, combined with an aqueous excipient composition including the t-butyl alcohol, amorphous sugar(s) and/or any desired optional excipients and/or surfactants in concentrations suitable to yield an aqueous suspension of particles as described above, and this suspension lyophilized to dryness. If desired, the particles can be collected by filtration or other means (e.g., centrifugation) prior to mixing with the aqueous excipient composition. If desired or necessary, solvent exchange prior to mixing with the aqueous excipient composition can be accomplished without collecting the particles by, for example, diafiltration, or other conventional means.

Although the method can be used with virtually any type of particles that have a propensity to aggregate and/or stick together, it has been discovered that the method is especially advantageous in the preparation of dry compositions of bilayered, hollow-cored particles, such as the bilayered protein coated polymeric nano- and/or micro-particles described in U.S. Pat. No. 6,193,951 and co-pending U.S. application Ser. No. 09/637,516 (WO 01/12071), the disclosures of which are incorporated herein by reference.

In a specific embodiment of the method, both t-butyl alcohol and one or more amorphous sugars are added to an aqueous suspension of such formed, bilayered, hollow-cored particles, either alone or in combination with one or more excipients, prior to lyophilization of the suspension. The suspension is then lyophilized to dryness to yield a dried particle composition that is readily dispersible upon addition of water. As is known in the art, the hollow-cored particles comprising the dry composition may be filled with a specified gas or mixtures of gases, such as nitrogen ($N_2$), air, or a perfluorocarbon, by filling the lyophilization chamber containing the dry particle composition with the specified gas or gases.

In another aspect, the present invention provides dry, readily dispersible and/or reconstitutable compositions of particles. The dry compositions are formed by lyophilizing an aqueous suspension of particles comprising t-butyl alcohol and/or an amorphous sugar(s) as described herein, and generally comprise particles and an amorphous sugar or mixture of two or more amorphous sugars in a weight ratio range of about 0.3:1 to 12:1 (for hollow-cored particles) or 0.02:1 to 0.86:1 (for solid-cored particles). The dry composition may optionally include one or more excipients and/or surfactants, as described above. The excipients may be included in the suspension prior to lyophilization, or they may be added to the dry, lyophilized composition. When included in the composition, such excipients are typically used in amounts commonly employed in particle compositions designed for therapeutic and/or diagnostic applications. In a specific embodiment, the composition comprises the following components with the indicated approximate weight to weight ratios (wt ingredient:wt particle):

| Ingredient | wt Ratio | |
| --- | --- | --- |
| | hollow cored | solid cored |
| Particles | | |
| Sucrose, NF | 1.5:1 | 0.11:1 |
| Polyethylene Glycol 3350, NF | 17.3:1 | 1.24:1 |
| Poloxamer 188, NF | 3.6:1 | 0.26:1 |
| Glycine, USP | 7.2:1 | 0.52:1 |

The dry composition may be packaged in any convenient packaging container, depending upon the particular application. For example, the dry composition may be packaged in bulk, permitting desired quantities to be measured out on an as-needed basis. Typically, the dry composition will be packaged in single use quantities in sealed glass vials of a size and configuration suitable for reconstituting the composition with water directly in the vial so that sterile conditions can be maintained. Vials of hollow-cored, gas-filled particles, may be stored in the vials or other similar containers under a headspace containing the tiller gas(es) such that the gas(es) in the cores do not diffuse out during storage.

DETAILED DESCRIPTION

The present invention provides methods and suspensions for forming compositions of particles that are less susceptible to particle aggregation than currently available methods and/or compositions. The methods and suspensions are useful in forming particle compositions for use in diagnostic imaging, drug delivery, and other medical and pharmaceutical applications. Also provided are dried particle compositions formed by the methods. Such dry compositions are readily dispersible in water, making them ideally suited for diagnostic and therapeutic applications. The methods are particularly advantageous for handling suspensions of particles comprising polymers and/or proteins, as well as other particles that have a propensity to aggregate or "stick together" during lyophilization, storage, and/or reconstitution. Among their numerous potential applications, the methods and suspensions are useful in the preparation of solid-cored or "matrix" particles comprising polymers and/or proteins, such as those disclosed in, for example, U.S. Pat. No. 5,558,857, U.S. Pat. No. 5,670,135, U.S. Pat. No. 5,674,468, U.S. Pat. No. 6,264,959, U.S. Pat. No. 6,177,062 and U.S. Pat. No. 5,565,215, and hollow-cored particles comprising polymers and/or proteins, such as those disclosed in U.S. Pat. No. 6,193,951, U.S. Pat. No. 6,200,548, U.S. Pat. No. 6,123,922, U.S. Pat. No. 6,333,021, U.S. Pat. No. 6,063,362, U.S. Pat. No. 6,022,252, U.S. Pat. No. 6,569,405, U.S. Pat. No. 6,045,777 and in co-pending U.S. application Ser. No. 09/637,516 (WO 01/12071). The particles, whether solid-cored or hollow-cored, will typically have diameters in a size range suitable for passing through the circulatory system (and avoiding accumulation by the RES). Typically, the diameters of the particles will be less than 10 µm, and the collection of the particles comprising a composition will have a relatively narrow distribution of average diameters. Particles suitable for administration via intravenous injection typically will have a numeric mean diameter in the range of 3-3.5 microns, with greater than 95%, and preferably greater than 99%, having diameters of less than 7 microns.

The methods are broadly applicable to the preparation of dry compositions containing a wide variety reconstitutable particles. In general, a method is provided for preparing aqueous particle suspensions in which particle aggregation problems are substantially reduced. This method is useful for any particles that have a propensity to aggregate during lyophilization, storage, and/or reconstitution, and generally involves lyophilizing to dryness an aqueous suspension comprising from about 0:3 mg to 4 mg of hollow-cored particles (weight is based upon the weight of the shell material) per milliliter of suspension or from about 0.3 mg to 56 mg solid-cored particles per milliliter of suspension and one or both of t-butyl alcohol and an amorphous sugar (or mixture of two or more amorphous sugars) in specified weight to weight ratios, depending upon whether the suspension comprises hollow-cored or solid-cored particles. For hollow-cored particles, the amorphous sugar(s) is typically included in the suspension at a weight to weight ratio (total weight amorphous sugars:wt particles) in the range of about 0.3:1 to 12:1 and/or t-butyl alcohol is included in the suspension at a weight to weight ratio (wt t-butyl alcohol:wt particles in the range of about 30:1 to 600:1. In a specific embodiment, the weight to weight ratio of total amorphous sugar(s) is in the range of about 0.75:1 to 3:1 and/or the weight to weight ratio of t-butyl alcohol is in the range of about 60:1 to 150:1.

For solid-cored particles, the amorphous sugar(s) is typically included in the suspension at a weight to weight ratio in the range of about 0.02:1 to 0.86:1 and/or t-butyl alcohol is included in the suspension at a weight to weight ratio in the range of about 2.14:1 to 43:1. In a specific embodiment, the weight to weight ratio of total amorphous sugar(s) is in the range of about 0.07:1 to 0.36:1 and/or the weight to weight ratio of t-butyl alcohol is in the range of about 4:1 to 11:1.

In a specific embodiment, the suspension includes both t-butyl alcohol and an amorphous sugar(s) in the disclosed weight to weight ratio.

"Amorphous sugars," as used herein, are those sugars that, while capable of crystallizing, can be trapped in a non-crystalline, amorphous state when lyophilized. These lyophilized amorphous sugars can spontaneously convert to a crystalline form if exposed to temperatures in excess of their glass transition temperature ($T_g$). Therefore, amorphous sugars useful in the present invention are those that have a relatively high glass transition temperature ($T_g$), typically above approximately 20° C. Specific examples of amorphous sugars suitable for use as described herein include, but are not limited to, sucrose, trehalose and lactose. The amorphous sugar(s) and/or t-butyl alcohol may be added during the particle formation or purification process as an additive in one or more oldie solutions carrying the particles or other aqueous compounds that form the particles. More typical is for the amorphous sugar(s) and/or t-butyl alcohol to be added as part of an excipient or composition solution that is combined with a particle suspension after particle formation.

The amorphous sugar(s) in the disclosed concentration ranges functions as an aggregation inhibitor in the lyophilization, storage, and/or reconstitution processes. At an amorphous sugar concentration substantially below the disclosed range, particulate aggregation may cause problems in forming a composition of discrete, reconstitutable particles. If the amorphous sugar concentration is too high, solvent removal may be unacceptably hindered. Solvent removal difficulties are a substantial concern in the preparation of hollow-cored particles, such as for instance bilayered, hollow-cored protein-coated polymeric particles, as described in U.S. Pat. No. 6,193,951 and co-pending U.S. application Ser. No. 09/637,516 (WO 01/12071).

The use of t-butyl alcohol in the disclosed concentration ranges provides dual benefits. In the disclosed concentration ranges, t-butyl alcohol acts to reduce the tendency of the particles to aggregate while enhancing solvent removal. The reduced aggregation effect is most pronounced when t-butyl alcohol is used in combination with an amorphous sugar as described above. In general, t-butyl alcohol has properties that result in it being almost completely removed from the suspension during lyophilization, making it particularly advantageous for use as a non-aggregation agent in making dry particle compositions suitable for in vivo administration to animals and humans. DMSO, or a mixture of DMSO and t-butyl alcohol, may also be used to similar effect.

Additional excipients may also be added to the aqueous particle suspension, either as further constituents of an excipient solution added after particle formation or during or before the particle formation step or steps. These excipients may include surfactants, such as poloxamers or tweens; bulking agents such as mannitol, lactose, or glycine; buffering agents such as acetate, citrate, or phosphate; collapse temperature modifiers such as dextran, polyethylene glycol, or sugars; crystalline matrix components such as mannitol or glycine; tonicity and osmolality modifiers such as mannitol, glycine, or sodium chloride, among others.

The formed particle suspension containing an amorphous sugar and/or t-butyl alcohol in the above-disclosed weight ratio ranges may be lyophilized to form a dry, reconstitutable particle composition. Lyophilization removes a substantial fraction of the water and the t-butyl alcohol and other processing solvents that may be present either in the suspension or within the particles. Hollow-cored particles can be filled with a gas or mixture of gases by flooding the lyophilization chamber with the gas(es). The lyophilized composition may be conveniently stored and/or transported in vials or some other suitable container. If the particles are gas-filled, they can be stored under the gas(es) used to fill the particles. Prior to use, the composition may be reconstituted with water to form a discrete suspension of particles having a physiologically compatible osmolality and pH.

In one embodiment, the reconstituted suspension advantageously comprises suspended particles in a concentration range of approximately 0.3 to 6 mg of hollow-cored particles or 0.3 to 84 mg solid-cored particles per milliliter (mL) (for hollow-cored particles the weight is based upon particle shell weight). In another embodiment, the aqueous particle suspensions, dry lyophilized particle compositions and reconstituted particle compositions include, in addition to the particles, amorphous sugar(s) and/or t-butyl alcohol (for the aqueous particle suspension), glycine, polyethylene glycol, and/or poloxamer 188 in the following concentration ratios:

| Excipient | wt:wt Ratio (wt excipient:wt particles) | |
| --- | --- | --- |
| | Hollow-cored particles | Solid-cored particles |
| Glycine | 0:1 to 75:1 | 0:1 to 6:1 |
| polyethylene glycol (MW 2000 to 6000) | 6:1 to 300:1 | 0.4:1 to 22:1 |
| poloxamer 188 | 0:1 to 60:1 | 0:1 to 4.5:1 |

The methods described herein are of particular advantage in preparing hollow-cored, bilayer polymeric particles having a proteinaceous outer layer or shell, such as those described in U.S. Pat. No. 6,193,951 and in co-pending U.S. application Ser. No. 09/637,516 (WO 01/12071), the disclosures of which are incorporated herein by reference. The specific, exemplary applications described below are focused on injectable compositions of microparticles and nanoparticles as described in these references. In general, however, any type of particle suspension, and in particular any biologically-compatible particle suspension, that is susceptible to problems caused by undesirable particle aggregation may be prepared as described herein.

In one exemplary embodiment, the particles comprising the lyophilizable aqueous suspension and dry, reconstitutable composition have a bilayered shell enclosing a hollow core. The outer layer of the shell may be formed of a protein or other biologically compatible amphiphilic material, such as, for instance, cross-linked albumin. The outer layer forms the surface of the particle which is exposed to the blood and tissues within the body. The inner layer may be a synthetic polymer or a synthetic biodegradable polymer, such as, for instance, poly(D,L-lactide). For use as ultrasound contrast agents, the cores of the particles may be filled with a gas, such as air, nitrogen or a perfluorocarbon. Particles are constructed such that the majority comprising the suspension or composition will have diameters within the range of about one to ten microns in order to past through the capillary system of the body. Alternatively, the particles may be constructed with diameters below 1 µm, such as for instance in the range of 200 to 800 nm, for use in imaging of or delivering a pharmaceutically active agent to, the lymph node system.

Since these particles have a shell comprising an outer and inner layer, the layers may be tailored to serve different functions. The outer, exposed layer serves as the biological interface between the particles and the body. The outer layer therefore generally comprises a biocompatible material that may be amphiphilic—having both hydrophobic and hydrophilic characteristics. The outer layer may also be formed of one or more synthetic biodegradable polymers. In addition to being amphiphilic, the outer layer may also have chemical features that permit charge and chemical modification. The inner layer comprises a biodegradable polymer, which may be a synthetic biodegradable polymer. The inner layer provides or enhances mechanical or drug delivery properties to the particle which may not be sufficiently provided by the outer layer. Because the outer layer provides a biologically compatible interface, selection of the polymer may be made without being constrained by surface property requirements. The polymer may be selected for its modulus of elasticity and elongation, which define the desired mechanical properties. Typical biodegradable polymers suitable for use as the inner layer of such bilayered particles are described in U.S. Pat. No. 6,193,951 and co-pending U.S. application Ser. No. 09/637,516 (WO 01/12071), the disclosures of which are incorporated herein by reference. Additional suitable biodegradable polymers are described in Langer, et al. (1983) *Macromol. Chem. Phys.* C23, 61-125, incorporated herein by reference. These various polymers can also be used to make solid-cored particles, which can be optionally coated with an outer layer of biocompatible, optionally amphiphilic, material, as described above.

For particles used as ultrasonic contrast agents or as a targeted, ultrasonically released drug earlier agent, the inner layer typically has a thickness no greater than that necessary to meet the minimum mechanical or drug carrying/delivering properties. This maximizes the interior gas volume of the particles. The greater the gas volume within the particles the better their echogenic properties. The combined thickness of the outer and inner layers of the particles depends, in part, on the mechanical and drug carrying/delivering properties required of the particles, but typically the total shell thickness will be in the range of 10 to 750 nm.

Briefly, these particles may be formed by a method comprising the following general steps. Two solutions are prepared, the first being an aqueous solution of the outer layer biomaterial. The second is a solution of the polymer ("polymer solution") which is used to form the inner layer, in a relatively volatile water-immiscible liquid which is a solvent for the polymer ("polymer solvent"), and a relatively non-volatile water-immiscible liquid which is a non-solvent for the polymer ("polymer non-solvent"). The polymer solvent is typically a C5-C7 ester, such as isopropyl acetate. The polymer non-solvent is typically a C6-C20 hydrocarbon such as decane, tridecane, cyclohexane, cyclooctane, and the like. In the polymer solution, the polymer and the water-immiscible solvents are combined so that the polymer fully dissolves and the two solvents are miscible with agitation. The polymer solution (organic phase) is slowly added to the biomaterial solution (aqueous phase) with agitation to form an emulsion. The relative concentrations of the solutions and the ratio of organic phase to aqueous phase utilized in this step and the degree of agitation essentially determine the final particle size and shell thickness. After thorough mixing of the emulsion, it is dispersed into water and typically warmed to about 30-35° C. with mild agitation. A cross linking agent, for example a carbodiimide or a bifunctional aldehyde such as glutaraldehyde, is added to the mixture to react with the biomaterial envelope to render it water insoluble, stabilizing the outer layer.

The inner core of the newly formed outer layer contains a solution comprising the polymer, the polymer solvent and the polymer non-solvent, each of which have different volatilities. As the more volatile polymer solvent evaporates or is diluted, the polymer precipitates in the presence of the less volatile polymer non-solvent. A film of precipitate is thus formed at the interface with the inner surface of the biomaterial (outer) layer. This precipitate forms the inner layer of the particle as the more volatile polymer solvent is reduced in concentration either by dilution, evaporation, or the like. The core of the formed particle contains predominately the polymer non-solvent.

At this stage, the formed particles are collected and formulated into an aqueous suspension including one or both of t-butyl alcohol and one or more amorphous sugars at the disclosed concentration ranges for hollow-cored particles, as well as any optional desired excipients and/or surfactants. The aqueous suspension may be prepared by suspending formed particles collected by centrifugation, filtration or other means in an aqueous solution comprising the desired amounts of t-butyl alcohol, amorphous sugar(s), and optional excipients and surfactants. Alternatively, the solvent system of the formed particles can be changed to a suspending medium by, for example, diafiltration or dilution (or other means or combination of means) and the t-butyl alcohol, amorphous sugar(s) and any desired excipients and/or surfactants dissolved in the aqueous solvent system to provide an aqueous particle suspension according to the invention.

This aqueous suspension is then dried by lyophilization, yielding a dry, reconstitutable particle composition that is typically in the form of a lyophilized cake. Inclusion of the amorphous sugar in the aqueous particle suspension that gets lyophilized minimizes particle aggregation in the lyophilized product. Inclusion of t-butyl alcohol further deters particle aggregation that occurs after reconstitution of the lyophilized, dry composition. The amorphous sugar remains in the dry, lyophilized particle composition, while the bulk of the t-butyl alcohol is removed. Use of these additives, whether during particle formation, processing of the suspension or as excipients added to a suspension of particles just prior to lyophilization, tends to provide a lyophilized cake having a high porosity and surface area. These additives may also increase the drying rate during lyophilization by providing channels for water and solvent vapor to be removed. They may also provide a lyophilized cake having a higher surface area than a lyophilized product prepared without them, which is beneficial in later reconstitution steps.

As previously disclosed in U.S. Pat. No. 6,193,951 and co-pending U.S. application Ser. No. 09/637,516 (WO 01/12071), aggregation of these bilayered particles during formation may be further minimized by maintaining a pH of at least one to two pH units above or below the isoelectric point ($P_i$) of the biomaterial forming the outer surface. As an alternative, the particles may be formulated at or near the $P_i$ with the use of surfactants to stabilize against excessive aggregation. In any event, buffer systems of the dry, lyophilized composition to be injected into the subject should be physiologically compatible.

The dry, lyophilized particle composition may be provided in unit containers containing a total weight in the range of approximately 1 to 50 mg of hollow-cored particles or 1 to 700 mg of solid-cored particles per container. Particles for use as ultrasonic contrast agents for imaging the circulatory system typically have a mean diameter of approximately 3 microns with the size range of approximately 1 and 10 microns. Typically, less than 5% of the particles will have a diameter greater than approximately 10 microns. Alternatively, particles for ultrasonically imaging the lymphatic system may have average diameters in the range of approximately 200 to 800 nm as described in co-pending U.S. application Ser. No. 09/637,516 (WO 01/12071).

Particles in a specific example of the present invention have an outer layer of cross-linked albumin. The albumin may be human serum albumin cross-linked with a dialdehyde cross-linker, such as glutaraldehyde The particles also have an inner layer of poly(D,L-lactide) that encapsulates a hollow core which may be filled with a gas or mixture of gases (e.g., air, nitrogen, perfluorocarbons, etc.). For applications such as delivery of a drug or some other pharmaceutically active agent, the core may be filled with the drug. Alternatively, the inner layer may further comprise the drug if it is co-precipitated with the biodegradable polymer during formation of the inner layer as described below.

In a specific embodiment, the glutaraldehyde crosslinked albumin/polylactide particles are formulated into an aqueous suspension comprising t-butyl alcohol in the disclosed weight ratio, sucrose in the disclosed weight ratio and polyethylene glycol, glycine and a poloxamer (at weight ratios discussed further below) such that after lyophilization the particles in the dry, lyophilized composition are contained within a matrix of polyethylene glycol, glycine, sucrose and the poloxamer, such as for instance poloxamer 188. Poloxamer is a non-proprietary name used in conjunction with a numeric suffix for individually unique identification of products for which a food, drug or cosmetic use is likely.

Upon reconstitution, the product would typically contain approximately 0.3 to 6 mg of hollow-cored particles or 0.3 to 84 mg of solid-cored particles per milliliter, however it is understood that it is possible to add any amount of reconstitution media to provide a range of concentrations beyond what is disclosed herein. The reconstitution media further may be isoosmotic such that the final osmolality of the reconstituted product is essentially independent of the volume of reconstitution media used.

In a specific embodiment of the formation of the hollow-cored particles having an outer layer of crosslinked albumin and an inner layer of poly(D,L-lactide), a pH-adjusted aqueous solution containing the albumin comprising the outer layer is first prepared. In one embodiment, the pH is in the range of approximately 3 to 9, more specifically approximately 4. The albumin may be human serum albumin. The pH may be adjusted by addition of an acid, for example hydrochloric acid. The albumin concentration is typically in the range of approximately 4% to 10% by weight. Monodisperse emulsions are favored at concentrations above approximately 4% albumin by weight. Aggregation of the resultant particles may become a problem at concentrations above about 10% albumin by weight.

Next, an organic solution containing poly(D,L-lactide) and cyclooctane (polymer non-solvent) dissolved in isopropyl acetate (polymer solvent) is prepared and emulsified into the aqueous solution. In specific embodiments, the intrinsic viscosity of the poly(D,L-lactide) should be greater than about 0.15 dL $g^{-1}$ (0.5% in chloroform, 30° C.) to maintain the particle integrity. The concentration of the poly(D,L-lactide) is in the range of approximately 0.2 to 3% by weight of the solution to maintain a sufficient particle wall strength without causing excess difficulty in removing the cyclooctane polymer non-solvent during lyophilization. The ratio of isopropyl acetate to cyclooctane is in the range of approximately 30:1 to 3:1 by weight. The higher ratios favor thicker and/or stronger particle walls. However, use of too high a ratio may result in walls that are so thick that formation of the hollow particle core is impaired. Use of excessive cyclooctane may result in overly fragile particle walls that may rupture in the hydrostatic environment of the circulatory system.

The organic solution is emulsified into the aqueous solution using standard emulsification techniques, such as membrane emulsification. Typically, the emulsification is performed at about 30° C. under flow rate and pressure conditions sufficient to provide a droplet size of about 4 microns (volumetric). The organic to aqueous component ratio is in the range of approximately 0.3:1 to 3:1, and more typically approximately 1.62:1. Ratios near the upper end of this range favor particulate monodispersivity. However, the use of an excessively elevated ratio may result in an emulsion that is too thick for processing. Below the lower ratio, the volume of the container required may become a limiting factor, although if suitable containers are available, lower ratios may be used.

The emulsion is then diluted approximately 3 to 18-fold, preferably about 4.6 fold (with stirring) into a second aqueous solution containing a cross-linker, such as glutaraldehyde. The crosslinker is included in the second aqueous solution at a concentration sufficient to provide a weight to weight ratio (crosslinker:albumin) in the resultant diluted suspension in the range of about 0.05:1 to 1:1. For glutaraldehyde, a final crosslinker to albumin weight ratio in the range of about 0.2:1 yields good results. The pH of this aqueous solution may be adjusted to a desired usage, such as for example a pH in the range of about pH 6 to 10, preferably in the range of about pH7-8.

Following dilution, stirring is continued at 30° C. until the isopropyl acetate is substantially removed by evaporation. Poloxamer 188 is then dissolved into the aqueous suspension, typically, to a concentration of about 0.25% by weight.

The suspension is then terminally filtered to remove aggregates and polymeric debris and diafiltered with aqueous poloxamer 188 solution (0.25% by weight) to remove unreacted glutaraldehyde and unassociated albumin. The volume of the suspension may be adjusted by dilution with the aqueous poloxamer 188 solution to achieve the desired particle concentration range of 0.09 wt % to 1.2 wt % (0.9 to 12% mg/ml suspension). In a specific embodiment, the particle concentration is adjusted to 0.5 wt %.

A concentrated aqueous excipient solution is prepared separately and added to the particle suspension to yield an aqueous particle suspension according to the invention. The aqueous excipient solution contains t-butyl alcohol and/or one or more amorphous sugar(s), in a specific embodiment sucrose, at concentrations sufficient to provide resultant weight to weight ratios (wt ingredient:wt particles) of 30:1 to 600:1 (t-butyl alcohol) and 0.3:1 to 12:1 (sucrose), as previously described. In a specific embodiment, the aqueous excipient solution includes both t-butyl alcohol and sucrose at weight to weight ratios of 105:1 and 1.5:1, respectively.

The aqueous excipient solution may further include one or more excipients and/or surfactants, as discussed above. In a specific embodiment, the concentrated aqueous excipient solution additionally includes polyethylene glycol (PEG) having an average molecular weight in the range of approximately 2200 to 8000 (preferably about 3400; PEG 3350), a poloxamer (preferably poloxamer 188) and glycine in concentrations sufficient to yield weight to weight ratios (ingredient:particles) in the resultant aqueous suspension in the range of about 6:1 to 300:1 (PEG), 0:1 to 60:1 (poloxamer) and 0:1 to 75:1 (glycine), respectively. In a specific embodiment, these excipients are included in the concentrated aqueous excipient solution to yield weight to weight ratios in the resultant aqueous particle suspension of 17.3:1 (PEG), 3.6:1 (poloxamer) and 72:1 (glycine), respectively.

The particle suspension and concentrated excipient solution are combined under chilled conditions in a proportion of approximately 1 part suspension to 2 parts concentrated excipient solution. The suspension is then dispensed into containers such as vials, lyophilized to dryness and stoppered under reduced nitrogen pressure. The vials typically contain a useful unit amount of particles, typically from about 2 to 200 mg of hollow-cored particles or 2 to 2800 mg solid-cored particles per gram of dry, lyophilized composition.

The lyophilized composition may be reconstituted by addition of water (or other physiologically acceptable buffer) to form a physiologically acceptable, injectable suspension of microparticles having an osmolality in the range of approximately 200 to 300 mOs/kg. The dry, lyophilized composition according to this embodiment which includes hollow-cored particles has the following concentration ratios of its components:

| Ingredient | Ingredient wt./ Particle wt. Ratio | | |
|---|---|---|---|
| | Low | high | specific embodiment |
| Polyethylene Glycol, NF | 6:1 | 300:1 | 17.3:1 |
| Poloxamer NF | 0:1 | 60:1 | 3.6:1 |
| Amorphous sugar | 0.3:1 | 12:1 | 1.5:1 |
| Glycine, USP | 0:1 | 75:1 | 7.2:1 |

A typical dry, lyophilized composition including a useful unit amount of hollow-cored particles may have the following composition:

| Ingredient | mg/vial | % w/w |
|---|---|---|
| Polylactide/Albumin Particles | 5.0 | 3.3 |
| Polyethylene Glycol 3350, NF | 86.7 | 56.6 |
| Poloxamer 188, NF | 18.0 | 11.7 |
| Sucrose, NF | 7.5 | 4.9 |
| Glycine, USP | 36.0 | 23.5 |
| Total | 153.2 | 100.0 |

Vials or other closed and/or sealed vessels containing the dry, lyophilized particle composition have a good shelf life and are easily reconstitutable with water to form an injectable ultrasound imaging agent. For hollow-cored particles, the reconstituted suspension may contain the following ingredients in the following concentrations:

| Ingredient | mg/ml |
|---|---|
| Polylactide/Albumin Particles | 1.5-2.5 |
| Polyethylene Glycol 3350, NF | 43.35 |
| Poloxamer 188, NF | 9.0 |
| Sucrose, NF | 3.75 |
| Glycine, USP | 18.0 |
| Water for injection, USP | qs |

The reconstituted product is injected preferably by bolus or by infusion into the blood stream of the subject and then used in conjunction with one or more methods for diagnostic imaging and/or targeted drug or pharmaceutical delivery.

EXAMPLES

The following examples are provided by way of illustration and are not intended to limit the invention.

Example 1

This example demonstrates the ability of the amorphous sugar sucrose and/or t-butyl alcohol to reduce aggregation of hollow-cored glutaraldehyde crosslinked albumin/polylactide microspheres during lyophilization and reconstitution.

Preparation of Cyclooctane-Filled Hollow-Cored Albumin/Polylactide Microspheres.

An organic solution containing 48.4 gm poly(D,L-lactide) (inherent viscosity of 0.41 dL/gm at 0.5% in chloroform, 30° C.), 0.666 kg cyclooctane, and 4.450 kg isopropyl acetate was prepared by dissolution of the polymer in the solvent mixture. The organic solution was slowly added with stirring to 3.25 kg of a 5 wt % solution of USP grade human serum albumin which had been adjusted to a pH of 4.0 with 10% HCl. While maintaining a temperature of 30° C., the resulting mixture was circulated through a sintered stainless steel frit. This process yielded an oil-in-water emulsion having an average volumetric droplet size of about 4 microns. An aqueous solution containing 30 kg of a 0.1% aqueous solution of glutaraldehyde was prepared. The pH was adjusted to between 7.2 to 8.0 using 1N NaOH. Approximately 6.8 kg of the emulsion was next added with stirring to the bath. Stirring of the bath was continued at 30° C. with a stream of dry nitrogen gas passing over the mixture until the isopropyl acetate was substantially removed by evaporation (overnight). After removal of the isopropyl acetate, the suspension was cooled to 18° C. and poloxamer 188 was added to the resultant suspension in the amount sufficient to yield a final concentration of 0.25 wt %. The suspension was depth-filtered to remove microcapsule aggregates and polymeric debris. To remove excess glutaraldehyde, formed salts, and the unassociated albumin, the suspension was next concentrated down and then washed by diafiltration against approximately volumes of a 0.25 wt % aqueous solution of poloxamer 188 using a 0.65 micron hollow fiber TFF. The diafiltered suspension was diluted with aqueous poloxamer 188 (0.25 wt %) to yield a suspension having a microsphere concentration of 5 mg microsphere shell weight per gram of suspension. The size distribution of the microspheres in the diluted suspension was measured with a Malvern 2000 particle size analyzer and found to have a volumetric peak diameter of 3.86 microns.

Hollow Microsphere Formulation and Lyophilization.

Separately, four different aqueous solutions were prepared to serve as lyophilization excipients using ingredients and at concentrations (by weight) in accordance with the table below.

| Lyophilization | Formulation Designation | | | |
|---|---|---|---|---|
| Excipient Solution | 1 | 2 | 3 | 4 |
| tert-butyl alcohol | 26.25% | 26.25% | 0% | 0% |
| Polyethylene glycol | 4.34% | 4.34% | 4.34% | 4.34% |
| Glycine | 1.8% | 1.8% | 1.8% | 1.8% |
| Poloxamer 188 | 0.9% | 0.9% | 0.9% | 0.9% |
| Sucrose | 0.38% | 0% | 0.38% | 0% |
| Deionized water | 66.3% | 66.7% | 92.6% | 93.0% |

The diluted microsphere suspension was next formulated with the 4 prepared excipients at a ratio of 1 part suspension to 2 parts excipient solution by weight. The resulting formulations were each dispensed into 10 ml serum vials at 3 ml/vial and then lyophilized to a dry cake using an FTS Dura-Stop lyophilizer and capped under nitrogen. During this lyophilization process, the cyclooctane core of the microspheres was removed to render hollow nitrogen-filled microspheres.

Vials of the now dried suspension were reconstituted in 2 ml deionized water and the size distribution of the microspheres in the suspensions were next determined using a Malvern 2000 particle size analyzer. Results of the size measurements are shown in the table below. The derived statistics in the table are based upon a volumetric frequency histogram of microsphere size and represent an average over three vials.

| | Formulation #1 | Formulation #2 | Formulation #3 | Formulation #4 |
|---|---|---|---|---|
| Mode Diameter | 3.68 μm | 3.86 μm | 4.07 μm | 5.21 μm |
| Mean Diameter | 3.78 μm | 4.08 μm | 4.25 μm | 8.18 μm |
| $90^{th}$ percentile, d(v, 0.9) | 5.61 μm | 6.52 μm | 6.71 μm | 13.63 μm |
| % microsphere volumetric diameter >7 μm | 2.18% | 7.17% | 8.23% | 34.38% |

Results.

Figure 1A:
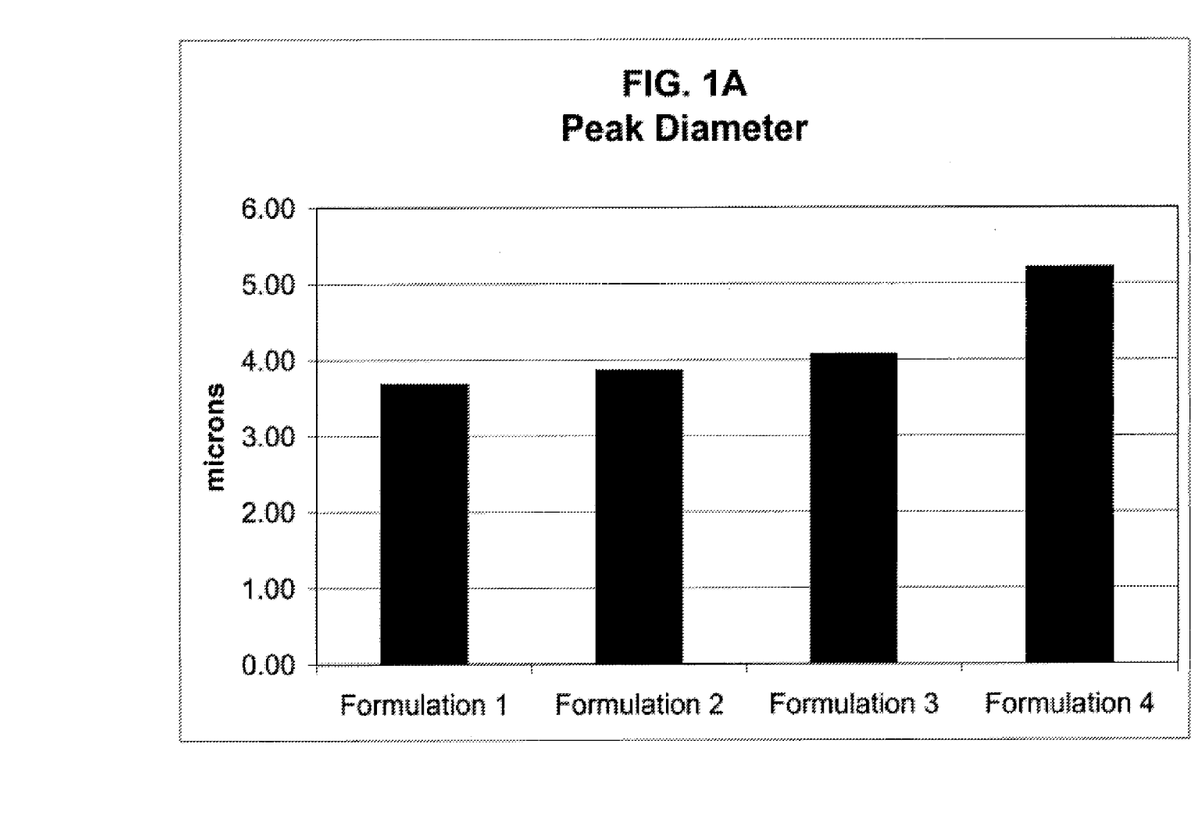
FIG. 1A provides a bar graph illustrating the peak diameters of hollow-cored microsphere compositions prepared as described in Example 1.
Figure 1B:
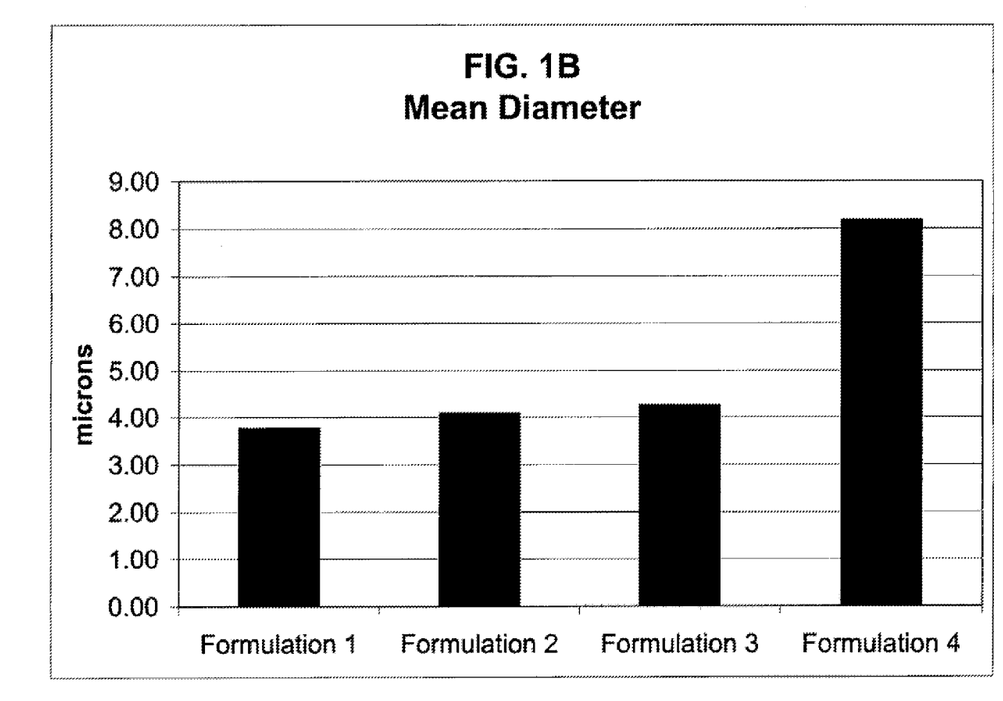
FIG. 1B provides a bar graph illustrating the mean diameters of hollow-cored microsphere compositions prepared as described in Example 1.
Figure 1C:
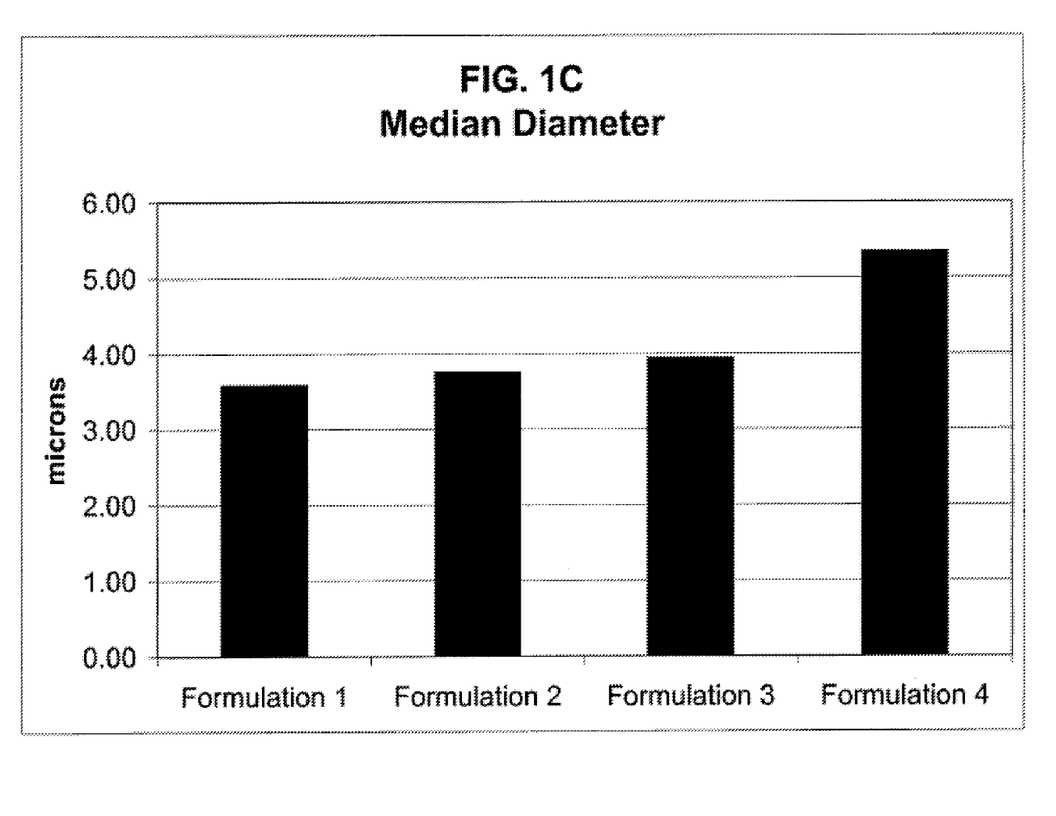
FIG. 1C provides a bar graph illustrating the median diameters of hollow-cored microsphere composition prepared as described in Example 1.
Figure 1D:
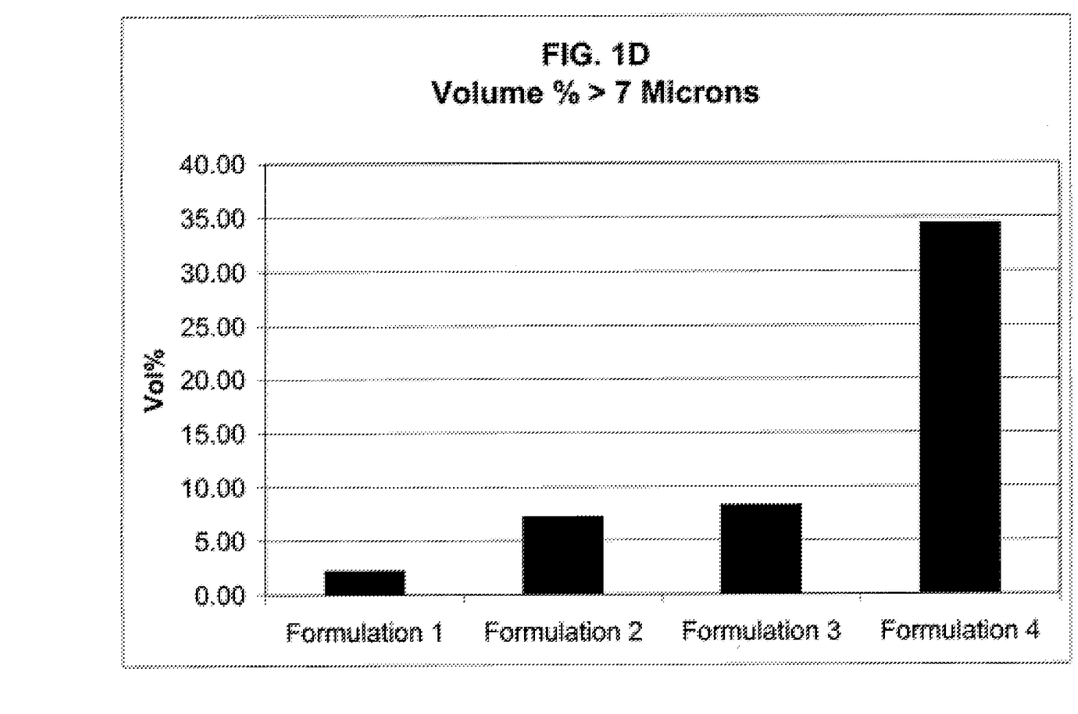
FIG. 1D provides a bar graph illustrating the volume percentage of microspheres having diameters greater than 7 microns for hollow-cored compositions prepared as described in Example 1.

An aggregate of microspheres will be interpreted by the particle size analyzer as a single larger microsphere. If aggregation of the microspheres is being reduced, it would be reflected by a size measurement that has shifted downward. Comparison of the size histogram statistics in the table (see FIGS. 1A-1D) reveals a trend toward smaller size microspheres and thus less aggregation in the suspensions that contain sucrose or tert-butyl alcohol in the formulation (formulations 2 & 3) over the formulation that contains neither ingredient (formulation 4). Also, there appears to be an additive effect to the reduction of microsphere aggregation when both sucrose and tert-butyl alcohol are present (formulation 1).

Microscopic inspection of formulation 1 and formulation 4 qualitatively confirmed the presence of a much greater degree of microsphere aggregation with formulation 4 than with formulation 1.

Example 2

The example demonstrates the ability of the amorphous sugar sucrose and/or t-butyl alcohol to reduce aggregation of solid-oared albumin-coated polylactide microspheres during lyophilization and reconstitution.

Preparation of Albumin-Coated Solid Polylactide Microspheres.

A 6% aqueous solution was prepared from a 25% solution of USP grade human serum albumin (HSA) by dilution with deionized water. The pH of the solution was adjusted to 4 using 6M HCl. Separately, a 10% solution of poly(D,L-lactide) was prepared by dissolution of the polymer into isopropyl acetate. The organic solution in the amount of 42 ml was slowly incorporated with stirring into 25 ml of the prepared HSA solution while maintaining a temperature of 30° C. The resulting coarse oh/emulsion was then circulated through a stainless steel sintered metal filter element. The emulsion was next diluted to 4× volume with deionized water and then added with stirring to 400 ml of deionized water maintained at 30° C. Immediately upon addition of the diluted emulsion, 1 ml of 25% glutaraldehyde and 2 ml of 1N NaOH were added to the stirring bath. Stirring was continued for approximately 3 hours until the isopropyl acetate had evaporated. After the 3 hours, 5 ml of a 15% solution of poloxamer 188 was added to the microsphere suspension. The microspheres were retrieved by centrifugation and washed 3 times using an aqueous solution of 0.25% poloxamer 188. The size of the microspheres were measured with a Malvern 2000 particle size analyzer and found to have a volumetric peak diameter of 4.34 microns.

Solid Polylactide Microsphere Formulation and Lyophilization.

The suspension of solid polylactide microspheres was diluted with 0.25% poloxamer 188 to achieve a microsphere concentration of approximately 2.5E+9 particles/ml. Separately, four different aqueous solutions were prepared to serve as lyophilization excipients using ingredients and at the concentrations (by weight) in accordance with the table below.

| Lyophilization Excipient Solution | Formulation Designation | | | |
|---|---|---|---|---|
| | 1 | 2 | 3 | 4 |
| tert-butyl alcohol | 26.25% | 26.25% | 0% | 0% |
| Polyethylene glycol | 4.34% | 4.34% | 4.34% | 4.34% |
| Glycine | 1.8% | 1.8% | 1.8% | 1.8% |
| Poloxamer 188 | 0.9% | 0.9% | 0.9% | 0.9% |
| Sucrose | 0.38% | 0% | 0.38% | 0% |
| Deionized water | 66.3% | 66.7% | 92.6% | 93.0% |

The diluted microsphere suspension was next formulated with the 4 prepared excipients at a ratio of 1 part suspension to 2 parts excipient solution, by weight. The resulting formulations were each dispensed into 10 ml serum vials and then lyophilized to a dry cake using an FTS Dura-Stop lyophilizer and capped under nitrogen.

Measurement of Particle Size.

After lyophilization, vials were reconstituted in 2 ml deionized water and the size distribution of the microspheres in the suspensions were determined using a Malvern 2000 particle size analyzer. Results of the size measurements are shown in the table below. The derived statistics in the table are based upon a volumetric frequency histogram of microsphere size and represent an average over three vials.

| | Formulation Designation | | | |
|---|---|---|---|---|
| | 1 | 2 | 3 | 4 |
| Mode Diameter | 5.66 μm | 5.99 μm | 7.28 μm | 9.48 μm |
| Mean Diameter | 6.22 μm | 7.77 μm | 8.06 μm | 12.75 μm |
| 90th percentile, d(v, 0.9) | 10.57 μm | 12.23 μm | 13.82 μm | 23.24 μm |
| % microsphere volume >10 μm | 12.2% | 17.6% | 25.2% | 45.4% |

Results.

Figure 2A:
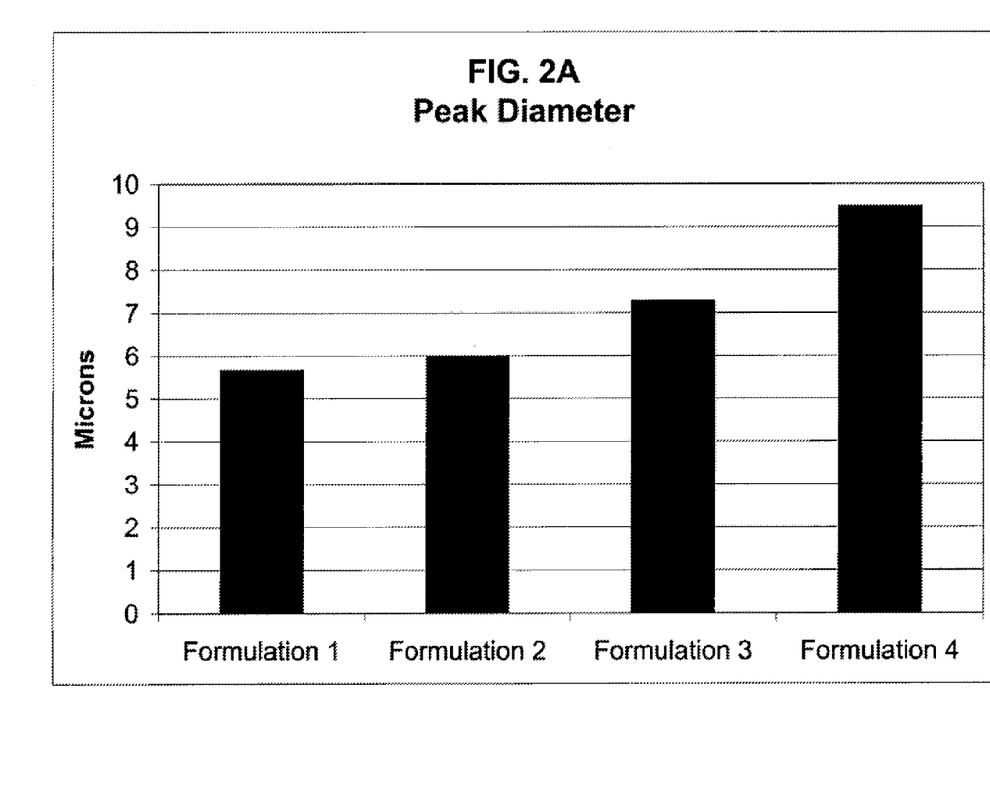
FIG. 2A provides a bar graph illustrating the peak diameters of solid-cored microsphere compositions prepared as described in Example 2.
Figure 2B:
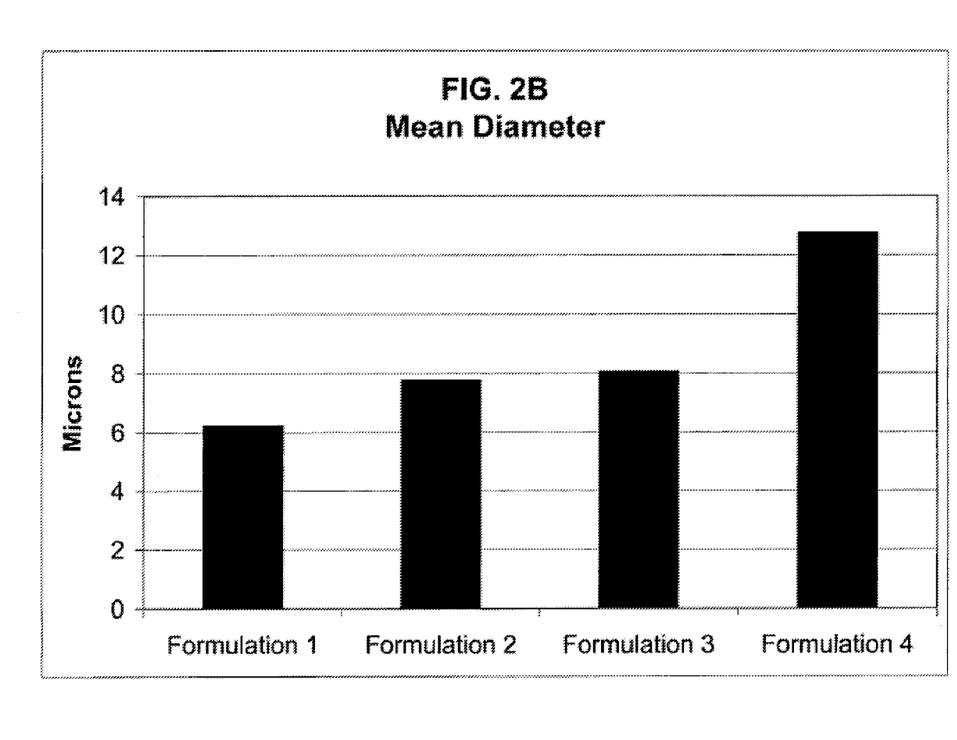
FIG. 2B provides a bar graph illustrating the mean diameters of solid-cored microsphere compositions prepared as described in Example 2.
Figure 2C:
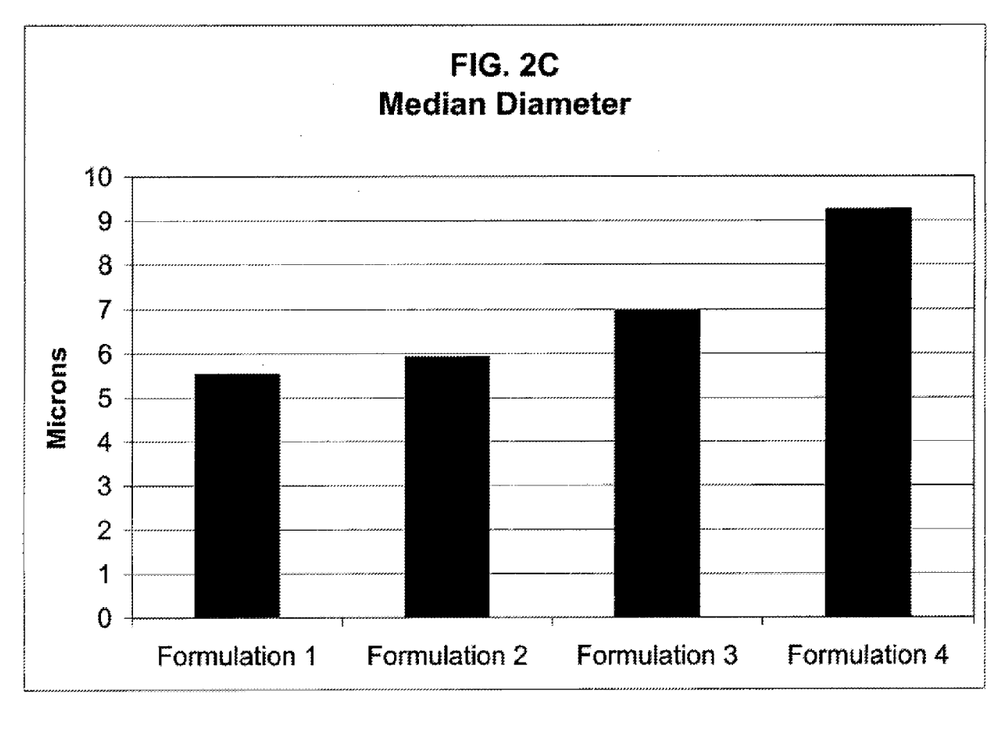
FIG. 2C provides a bar graph illustrating the median diameters of solid-cored microsphere compositions prepared as described in Example 2.
Figure 2D:
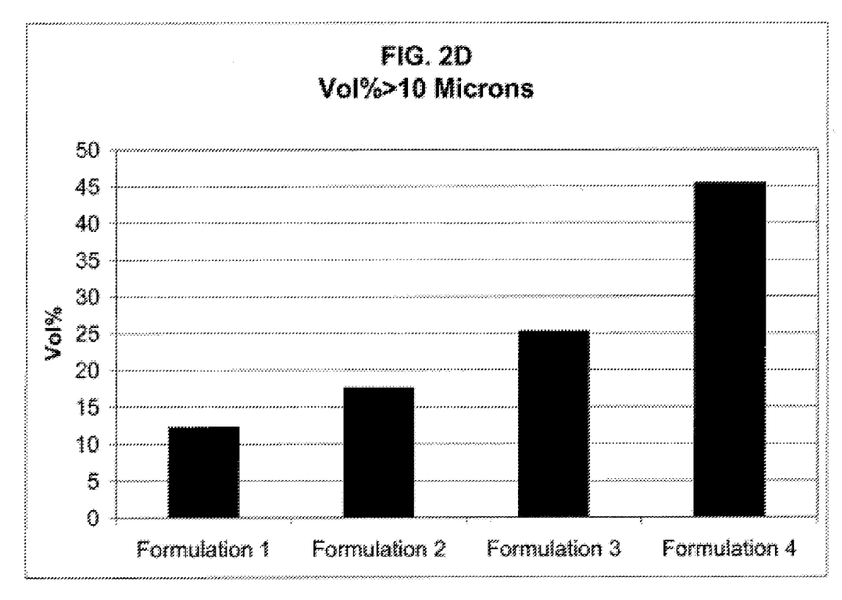
FIG. 2D provides a bar graph illustrating the volume percentage of microspheres having diameters greater than 10 microns for solid-cored compositions prepared, as described in Example 2.

An aggregate of microspheres will be interpreted by the particle size analyzer as a single larger microsphere. If aggregation of the microspheres is being reduced, it would be reflected by a size measurement that has shifted downward. Comparison of the size histogram statistics in the table (see FIGS. 2A-2D) reveals a trend toward smaller size microspheres and thus less aggregation in the suspensions that contain sucrose or tert-butyl alcohol in the formulation (formulations 2 & 3) over the formulation that contains neither ingredient (formulation 4). Also, there appears to be an additive effect to the reduction of microsphere aggregation when both sucrose and tert-butyl alcohol are present (formulation 1).

Example 3

This example demonstrates the effect of sucrose concentration on removal of residual solvent from the core of hollow-cored microspheres.

Cyclooctane filled microspheres were prepared as described in Example 1. Separately, four aqueous solutions, with increasing sucrose concentration, were prepared to serve as lyophilization excipients using ingredients and at concentrations (by weight) in accordance with the table below.

| Lyophilization Excipient Solution | Formulation Designation | | | |
|---|---|---|---|---|
| | 1 | 2 | 3 | 4 |
| tert-butyl alcohol | 26.25% | 26.25% | 26.25% | 26.25% |
| Polyethylene glycol | 4.34% | 4.34% | 4.34% | 4.34% |
| Glycine | 1.8% | 1.8% | 1.8% | 1.8% |
| Poloxamer 188 | 0.78% | 0.78% | 0.78% | 0.78% |
| Sucrose | 0.0% | 0.15% | 0.38% | 0.6% |
| Deionized water | 66.83% | 66.68% | 66.45% | 66.23% |

The diluted microsphere suspension was next formulated with the 4 prepared excipients at a ratio of 1 part suspension to 2 parts excipient solution by weight. The resulting formulations were each dispensed into 10 ml serum vials at 3 ml/vial and then lyophilized to a dry cake using a Virtis Ultra-35XL lyophilizer and capped under nitrogen. During this lyophilization process, the cyclooctane core of the microspheres was removed to render hollow nitrogen-filled microspheres.

Product vials were analyzed for residual cyclooctane by gas chromatography. The results are tabulated below,

| Formulation Number | Residual Cyclooctane (micrograms per vial) |
|---|---|
| 1 | 10.6 μg |
| 2 | 13.4 μg |
| 3 | 274 μg |
| 4 | 926 μg |

Example 4

This example demonstrates the effect of t-butyl alcohol concentration on removal of residual solvent from the cores of hollow-cored microspheres.

Cyclooctane filled microspheres were prepared as described in Example 1. Separately, five aqueous solutions, with increasing tart-butyl alcohol concentration, were prepared to serve as lyophilization excipients using ingredients and at concentrations (by weight) in accordance with the table below.

| Lyophilization Excipient Solution | Formulation Designation | | | | |
|---|---|---|---|---|---|
| | 1 | 2 | 3 | 4 | 5 |
| tert-butyl alcohol | 0% | 15% | 26.25% | 30% | 37.5% |
| Polyethylene glycol | 4.34% | 4.34% | 4.34% | 4.34% | 4.34% |
| Glycine | 1.8% | 1.8% | 1.8% | 1.8% | 1.8% |
| Poloxamer 188 | 0.78% | 0.78% | 0.78% | 0.78% | 0.78% |
| Sucrose | 0.38% | 0.38% | 0.38% | 0.38% | 0.38% |
| Deionized water | 92.58% | 77.58% | 66.33% | 62.58% | 55.08% |

The diluted microsphere suspension was next formulated with the 5 prepared excipients at a ratio of 1 part suspension to 2 parts excipient solution by weight. The resulting formulations were each dispensed into 10 ml serum vials at 3 ml/vial and then lyophilized to a dry cake using a Virtis Ultra-35XL lyophilizer and capped under nitrogen. During this lyophilization process, the cyclooctane core of the microspheres was removed to render hollow nitrogen-filled microspheres.

Product vials were analyzed for residual cyclooctane by gas chromatography. The results are tabulated below.

| Formulation Number | Residual Cyclooctane (micrograms per vial) |
|---|---|
| 1 | 1654 μg |
| 2 | 483 μg |
| 3 | 152 μg |
| 4 | 92 μg |
| 5 | 79 μg |

The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

What is claimed is:

1. A dry composition comprising:
   a) a plurality of hollow-cored microparticles in an amount of 3.3 wt %;
   b) polyethylene glycol 3350 in an amount of 56.6 wt %;
   c) poloxamer 188 in an amount of 11.7 wt %;
   d) sucrose in an amount of 4.9 wt %; and
   e) glycine in an amount of 23.5 wt %.

2. The dry composition of claim 1 in which the hollow-cored microparticles comprise a bilayered shell, the bilayered shell comprising an inner layer of poly(D,L)lactide and an outer layer of glutaraldehyde crosslinked albumin.

3. The dry composition of claim 1 in which the hollow core of the hollow-cored microparticles is filled with a gas or mixture of gases.

4. The dry composition of claim 3 in which the gas is nitrogen.

5. The dry composition of claim 4 which is packaged in a stoppered glass vial that is sealed under nitrogen.

6. The dry composition of claim 5 in which the glass vial contains 5 mg microparticles, 86.7 mg polyethylene glycol 3350, 18 mg poloxamer 188, 7.5 mg sucrose, and 36 mg glycine.

7. The dry composition of claim 1, wherein said composition is lyophilized to dryness and further comprises polymeric and/or proteinaceous particles.

* * * * *